United States Patent [19]

Reich et al.

[11] Patent Number: 4,459,023

[45] Date of Patent: Jul. 10, 1984

[54] ELECTRO-OPTIC INSPECTION SYSTEM FOR TRANSPARENT OR SEMITRANSPARENT CONTAINERS

[75] Inventors: Frederick R. Reich, Richland; Errol V. Allen, Benton City, both of Wash.

[73] Assignee: Kirin Beer Kabushiki Kaisha, Tokyo, Japan

[21] Appl. No.: 279,073

[22] Filed: Jun. 30, 1981

[51] Int. Cl.³ .......................................... G01N 21/88
[52] U.S. Cl. .................................. 356/237; 356/240; 250/223 B
[58] Field of Search ................... 356/237, 239, 240; 250/223 B, 572

[56] References Cited

U.S. PATENT DOCUMENTS

| | | | |
|---|---|---|---|
| 3,191,773 | 6/1965 | Wyman | 250/223 B |
| 4,030,830 | 6/1977 | Holly | 356/237 |
| 4,249,075 | 2/1981 | Loval et al. | 250/223 B X |
| 4,262,196 | 4/1981 | Smith | 250/223 B |
| 4,283,145 | 8/1981 | Miyazawa | 356/237 |

Primary Examiner—Vincent P. McGraw
Assistant Examiner—L. A. Dietert
Attorney, Agent, or Firm—Koda and Androlia

[57] ABSTRACT

In general, used beer, alcoholic drink or medical bottles are collected to be used again. Such used returnable bottles often have defects such as dust and contaminant or cracks, and they must be removed from the bottles before or after the bottle cleaning process. This invention positively satisfies such a requirement. The electro-optic inspection system according to this invention uses a polarized, scanned optical beam and an array of polaroid optical detectors and a logic signal processing system thereby to securely detect the defects on the transparent or semitransparent containers.

7 Claims, 13 Drawing Figures

FIG. 3
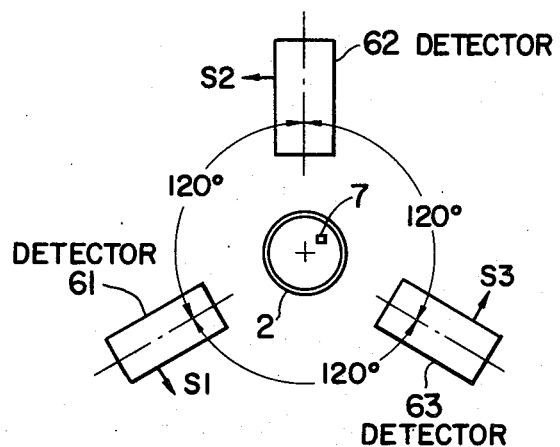
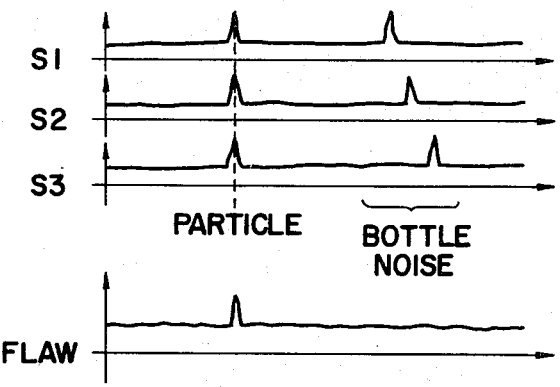
FIG. 5
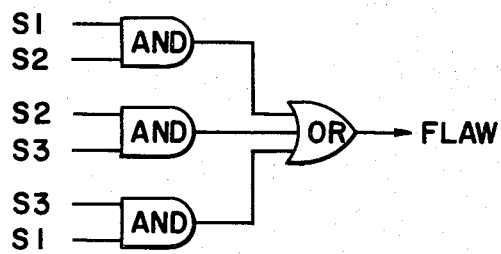

$\theta_1(t) = A(t) \cdot \sin(\omega t + \frac{\pi}{4})$ $\theta_2(t) = A(t) \cdot \sin \omega t$

ELECTRO-OPTIC INSPECTION SYSTEM FOR TRANSPARENT OR SEMITRANSPARENT CONTAINERS

BACKGROUND OF THE INVENTION

This invention relates to an electro-optic inspection system of transparent or semitransparent containers, such as glass and plastic bottles to be used as beer bottles, alcoholic drink bottles and so on, for the presence of contaminants and hazardous materials.

New bottles require inspection because of potential defects that form hazardous glass structures within the bottles, whereas bottles that are recovered from consumers and have been cleaned for re-use, require an inspection for liquid and solid contaminant materials. Reject bottles must be discriminated from the clean or flawless bottles because of their potential physical or biological hazard to the consumer and to maintain the quality of the products.

The detection of these internal glass defects (such as fragile glass filaments that can break off during the filling operation) and contaminants is not a simple task. The conventional use of human visual inspectors is subject to a wide range of human limitations such as establishing and maintaining an inspection baseline or reference and loss of detection reliability and sensitivity from human factors such as fatigue. Systems which employ the transmission of localized optical radiation (small diameter optical beams) in their inspection principle are sensitive to the imprecise structure of the glass container. For example, bottles which are fabricated by blow molding will have a variation in wall thickness as well as mold seam markings and mold identification numerals. Many bottle designs include embossed regions on the outer surface of the glass to enhance the bottle's structural integrity. These variations in the bottle's structure produce an optically noisy background against which a small contaminant particle or structural defect must be detected. The interference effects of this background noise is enhanced in inspection concepts that use imaging systems or transmit small diameter beams (e.g., laser beams) through the walls or bottom of the glass container in performing the inspection task. For example, a small diameter beam transmitting through the container will be refracted and reflected (resulting in an attenuation of the transmitted light) from these localized bottle structures. With an inspection system using an imaging system, the depth of focus is usually large enough to include both the inner and outer wall surfaces. This physical background is then almost impossible to separate from a contaminant particle without desensitizing the inspection response. The inspection of glass containers is further complicated when a permanent label is present on the container wall. The label forms a uniform background, blocking or scattering optical transmission. As a result, a labeled area on a semitransparent container usually receives a less than satisfactory inspection for the presence of contaminants or hazardous materials.

SUMMARY OF THE INVENTION

Accordingly, an object of this invention is to provide an electro-optic inspection system to effectively enhance the inspection of transparent or semitransparent containers. More specifically, an object of this invention is to provide an electro-optic inspection system in which the inspection reliability and area are improved in inspection systems that use optical transmission through the container walls or bottom. The foregoing object of this invention is achieved by the application of a polarized optical detector system and the use of multiple optical detectors with a polarized or scanned optical beam in an inspection system applied to the inspection of transparent or semitransparent containers with defects and contaminants.

The novel features of this invention are set forth in the appended claims. The nature, principle and utility of the invention will become more apparent from the following detailed description when read in conjunction with the accompanying drawings, in which like parts are designated by like reference numerals.

BRIEF DESCRIPTION OF THE DRAWINGS

In the accompanying drawings:

FIG. 3 is an explanatory diagram showing a typical embodiment of the multiple detection system according to this invention;

FIGS. 4A through 4D are time charts showing one operating example of the device in FIG. 3;

FIG. 5 is a logic circuit showing one example of the signal processing unit which carries out the operation shown in FIGS. 4A through 4D;

DETAILED DESCRIPTION OF THE INVENTION

As conducive to a full understanding of this invention, the basic differences in the interaction of polarized light with a smooth clean glass or plastic (dielectric) surface as contrasted with the interaction with a contaminant or hazardous material particle with forms the basis of this invention will be described.

A polarized light beam incident on a dielectric (glass or plastic) surface will experience reflection, scattering and refraction (for the transmitted light). The optical reflection and refraction are generally attributed to the bulk material properties (i.e., refractive index) whereas optical scattering occurs at an interface of two materials when there are abrupt slope changes in the interface plane. Here optical scattering will be produced from the roughness properties of the material surfaces forming the optical interface. A plane polarized beam reflected from an optically smooth dielectric material (glass or plastic) will be largely reflected or refracted as a plane polarized light. The principle angle of the polarization may be altered, but the polarization status will remain unchanged. For plane polarized light that is optically scattered from the same surface or from a localized abrupt change in refractive index, the polarization state will be altered and some form of elliptical polarization will be produced (circular polarization is considered as a special case of elliptical polarization). A further understanding of the principles of polarized light can be gained from any textbook on optics, such as Jenkins and White, "Fundamentals of Optics" (McGraw-Hill Book Co., Inc., New York, N.Y., 1957).

Figure 1:
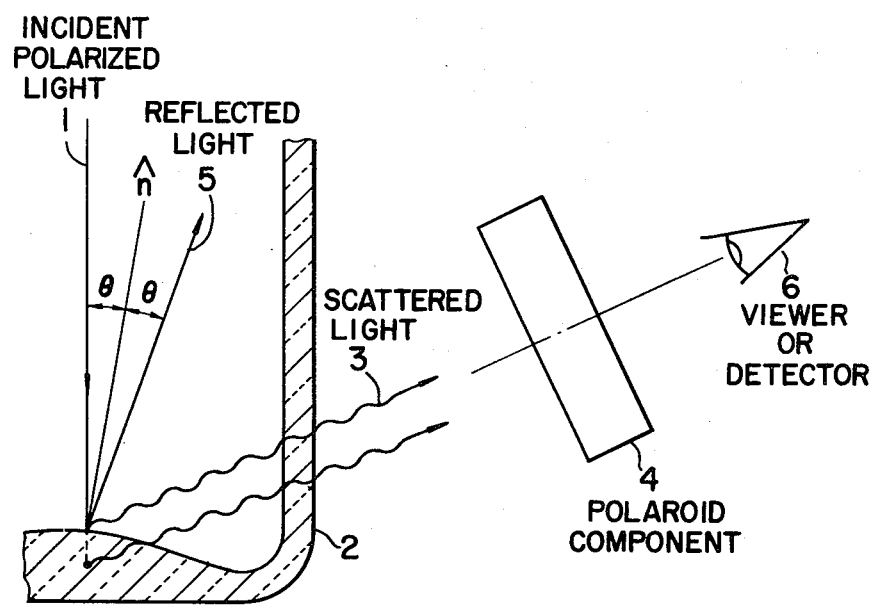
FIGS. 1 and 2 are schematic illustrations for explaining the concept of this invention.
Figure 2:
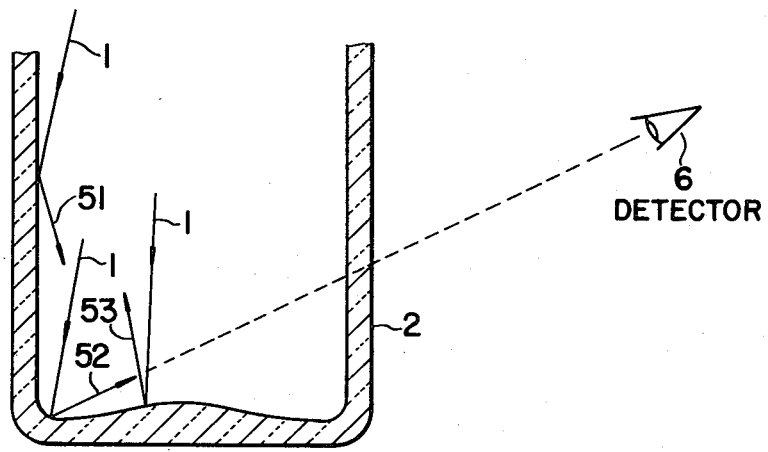

In FIG. 1, a linear polarized optical beam 1 is shown incident on the interior surface of a glass container 2. The glass surface will reflect some of this optical beam 1, with the same state of polarization as the incident beam following the optical laws of reflection (incident angle $\theta$ is equal to reflection angle $\theta$). The glass 2 will have some degree of surface roughness and inhomogeneous structure in the glass volume (in particular, small bubbles and contaminant particles) that will produce some optical scattering. This scattered light 3 will be slightly depolarized but the bulk of the incident light that is reflected or refracted in the glass 2, will retain its original polarization. If one views this scattered light 3 through an optical polarizer (such as a Nichol prism or sheet of commercial polarizing material) 4, the transmitted light intensity will vary when the polaroid component 4 is rotated about the viewing axis. A minimum will occur when the polaroid component pass-axis is positioned 90° to the polarization axis of the reflected or refracted optical beams. If the polarized beam 1 is incident on a contaminant particle (such as residual paper or mold) the scattered light 3 will be highly nonpolarized. A change in polarization will also be produced if the contaminant particle is a transparent, optically active material where the state of polarization of light transmitted through the particle is altered by the bulk properties of the material. Placing an optical detector at the viewing position, with an optical collecting system to increase the collecting field angle, produces an effective technique for inspecting glass or plastic containers for contaminant particles and hazardous glass materials. The polaroid component 4 must be positioned to minimize the optical signal from a "clean" container surface and in a position where the potential polarization altering effects of the collecting optical system will not affect the polarization state of this background light reaching the detector surface. The reflected light 5 from the container surface can exit at almost any angle as the incident beam 1 scans over the interior of the container 2. As shown in FIG. 2, there will be particular positions within a container 2 where the reflected beam 52 is directed into the optical detector 6. Where, the reference numerals 51, 52 and 53 show the surface reflected beams, respectively.

A polaroid component 4 will not transmit plane polarized light when the polarization axis of the light is at a 90° angle to the pass-axis of the polaroid component 4. The completeness of this light blockage depends on the polaroid material, pureness of the state of polarization of the incident light beam 1 and the field angle of the light incident on the polaroid component 4. In practice, a small amount of the reflected light from the glass surface will reach the detector 6 where it can potentially overwhelm the scattered light 3 (52) from a contaminant particle. As indicated in FIG. 2, with a beverage container there are only discrete positions where this problem could occur as an optical beam 1 scans over the interior of the container 2. By identifying these positions, the signal from the detector 6 can be gated off to eliminate these problem areas. Therefore, to inspect the full interior of a glass container 2, an array of detectors would be positioned circumferentially around the perimeter of the container 6. Since the optical scatter generally is non-directional and spreads over a near hemispherical surface, each detector will receive some scattered light 3 from a contaminant particle. The optical noise from reflections or refractions of a specific container area is highly directional and will only reach one detector, with each detector being sensitive to a different portion of the container 2. As an example, the detectors 61-63 in FIG. 3 would simultaneously receive light from the contaminant particle 7 but not from direct corner reflection as indicated in FIG. 2. The optical condition of beam position number 52, in FIG. 2, for a single small diameter scanning optical beam would be satisfied for only one detector at a time. By logically combining the three detector outputs (as shown in FIGS. 4A through 4D and FIG. 5), these optical problem areas can be eliminated and a response retained only for the contaminant particle 7. Where, FIGS. 4A, 4B and 4C show detector signals S1, S2 and S3 from the detectors 61, 62 and 63, respectively, and further FIG. 4D shows a flaw signal which is obtained as combined detector signal by a logic circuit shown in FIG. 5.

One potential method of signal processing is illustrated in FIG. 5. With this signal logic, a "flaw" response requires a simultaneous signal above the fixed threshold level from more than one detector. Since the background noise has been shown to be position dependent, each detector will see a different noise signal that will not be time coincident with another detector. While only three detectors 61-63 were used in this example to illustrate a potential signal processing concept, the addition of more detectors would allow much more sophisticated signal processing system. This system would be capable of exercising further advantages of the most sensitive regions for each detector and produce a more complete rejection of signals not generated by contaminant particles.

Figure 6:
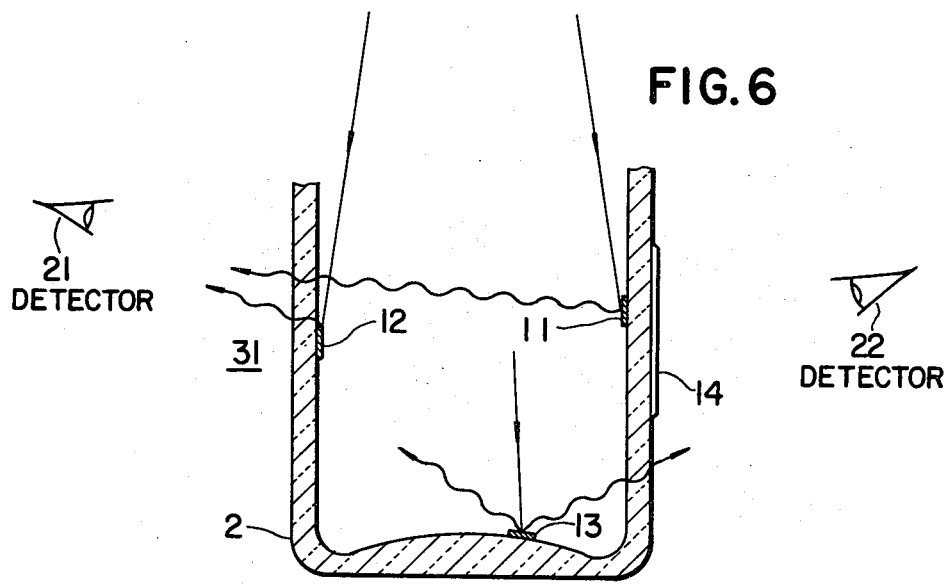
FIG. 6 is an explanatory diagram showing the scattered beams from articles and the arrangement of detectors.

With an optical beam that scans the entire inner surface of a beverage container (bottom corners and walls), areas not accessible to through transmission inspection can be covered, such as behind a permanent label. As indicated in FIG. 6, the scattered light 31 from particles 11 and 12 are partially blocked by the opaque label 14 and will not reach both detectors 21 and 22. However, light from particle 13 can reach both detectors 21 and 22. By arranging multiple detectors around the perimeter of the glass container 2, more than one of the detectors would receive scattered light from a contaminant particle even if the particle is located behind the label region. Signal processing could then be used to indicate the presence of contaminant material even against a high background of scattered light from a label area.

The subject matter of this invention resides in the application of a scanned polarized optical beam, with optical multiple-detectors that are sensitive to polarization thereby to detect contaminants and other hazardous material on or in semitransparent containers.

Figure 7:
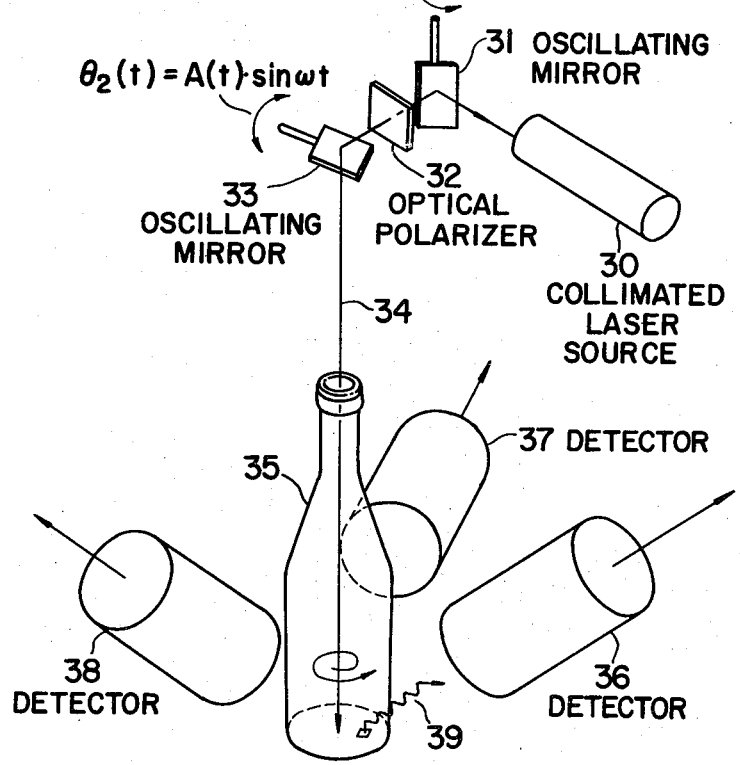
FIG. 7 is a schematic diagram showing one example of this invention.

One embodiment of this invention shown in FIG. 7 uses a spiral scanned beam 34 with three separate optical detectors 36-38 and a signal processing network which includes signal coincidence logic as shown in FIG. 5. The spiral beam scan 34 can be produced with one of several conventional electro-optical or mechanical techniques. The container scan can be produced by using a stationary container with a moving beam to scan its interior or a moving container (rotating) and a stationary beam or a line scanned beam with a rotating container. The objective of the scanning system is to cover the total areas of the interior of the container. The spiral scan concept can be implemented in at least two very common ways, one using an orthogonal arrangement of oscillating mirrors (torsional motors with mirrors) 31 and 33 as shown in FIG. 7 and another method using an optical rotating element (such as a Dove prism) and a single oscillating mirror. In the first method, the two mirrors 31 and 33 are driven with amplitude ramped sinusoidal signals $\theta_1(t)=A(t)\cdot\sin(wt+\pi/4)$ and $\theta_2(t)=A(t)\cdot\sin wt$ that have a 90° phase difference between the two mirror motors. With a constant driver amplitude this will produce a circular pattern, but with a saw tooth amplitude, an expanding or collapsing spiral pattern is produced. In the second method, the deflecting mirror produces a radial deflection while the otpical rotating element produces the circular scan. With the proper velocity and phase between the mirror and rotating element driver, a spiral beam scan can be produced. By changing the phase and velocity of the scanning elements, one can also produce a rotating, scanned line that is centered about the interior of the glass container 35.

In FIG. 7, the polarized optical beam 34 is shown being generated with a collimated laser source 30 and polarizing element 32. A similar polarized beam can be produced using a laser with inherent beam polarization or with an arc lamp or filament source, collimating optics and a polarizing component. In this embodiment, oscillating mirrors 31 and 33 with their sinusoidal drivers will produce a spiral scan over the interior of the container 35. The three detectors 36–38 are positioned around the container perimeter to intercept a maximum amount of scattered light 39 from the container interior. Each optical detector (36, 37, 38) has a polaroid component through which all light reaching the detector must pass and collecting optics to increase its field of reception for scattered light 39. The light sensitive component of the detector could be a solidstate detector or a vacuum tube photo-multiplier detector. The only requirements for this optical element are sensitivity to a wavelength region which includes the illuminating beam source emission 34 and an electrical response that can follow the actual intensity changes when small contaminant particles are intercepted by the optical beam. The detectors 36–38 in FIG. 7 also contain an optical band-pass filter centered at the laser wavelength to reduce the ambient light level reaching the detector.

Figure 8:
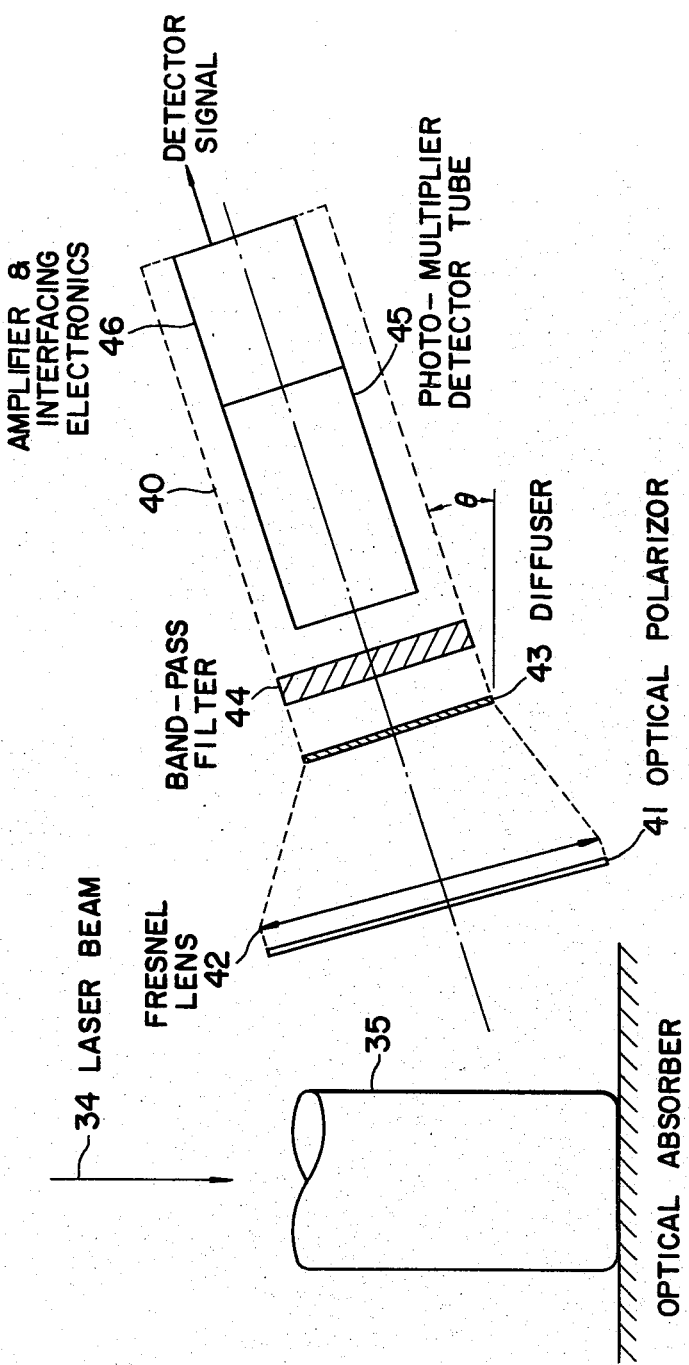
FIG. 8 is a diagram for explaining the photo-multiplier detector according to this invention.
Figure 9:
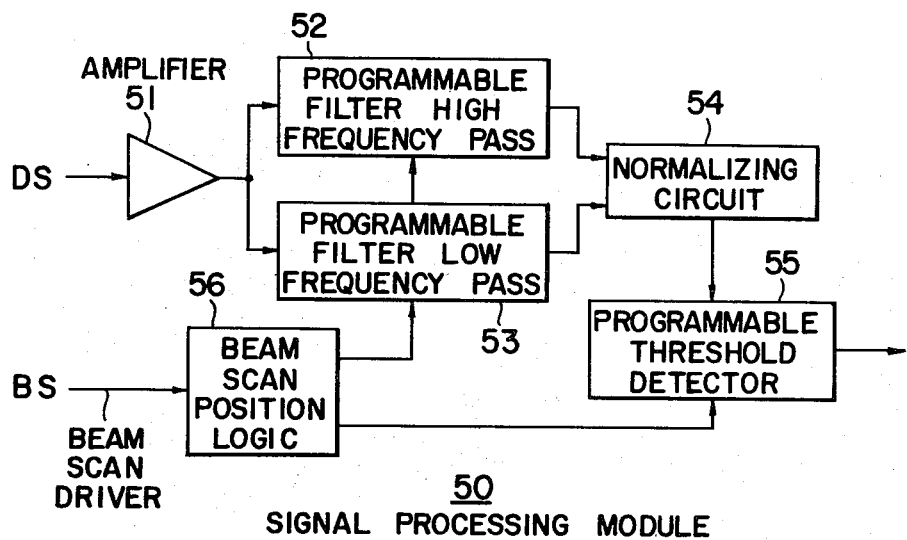
FIG. 9 is a block diagram showing one example of the signal processing circuit according to this invention.
Figure 10:
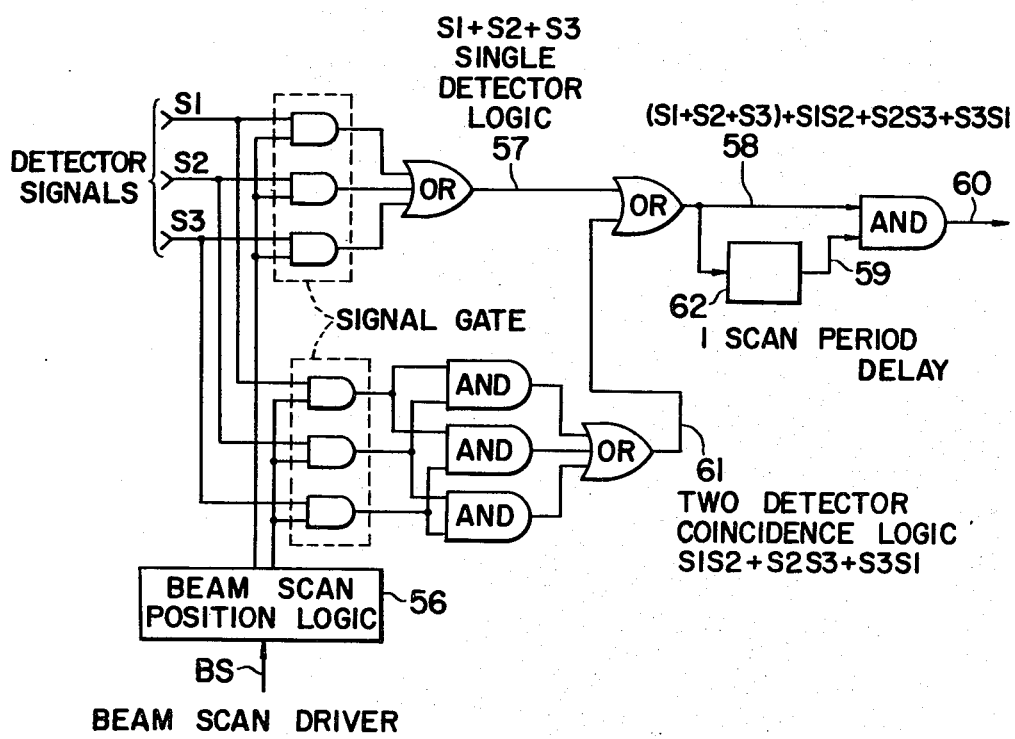
FIG. 10 is a logic circuit showing one example of the threshold detector shown in FIG. 9.

One embodiment of a detector would use a Fresnel lens 42 for optical collector, He-Ne laser band-pass filter 44 and photo-multiplier detector 45 as shown in FIG. 8. The axis of the detector 40 is set at an angle $\theta$ to increase the view of the bottom area and still maintain good optical collection for the wall areas. A Fresnel lens 42 images the central area of the bottle on the diffuser surface. To produce a uniform light intensity over the detector surface, an optical diffuser 43 is used (opal glass or translucent plastic) to scatter the image light. If the incident (laser) light beam 34 in the container 35 is very intense and the ambient light eliminated, the bandpass filter 44 will not be necessary in the detector system. Depolarized light from contaminant particle optical scatter will pass through the polaroid component 41 and be focused by the Fresnel lens 42 near the diffuser component surface. The detected signal is amplified and input to the signal processing module 50, as indicated in FIG. 9. The detector signals DS are amplified by an amplifier 51 and then the low frequency signal components from a low-pass frequency filter 53 removed with a high-pass frequency filter 52. The filter cutoff frequency is set to produce a maximum signal response from a small (0.5–1.0 mm diameter opaque particle) contaminant particle. The specific frequency parameters depend on the scanning velocity of the scanned beam. With a spiral scan pattern, this velocity is not constant and it may be necessary to use multiple signal processing channels to produce an optimum signal contaminant particle signal over the interior of the container. The filtered signals are then amplitude normalized by dividing the low frequency (dc) component into the high frequency (ac) component with a normalizing circuit 54. This normalizing function can be implemented with either digital or analog electronic techniques. Those skilled in either digital or analog techniques will understand specifically how to implement both the filtering and the normalizing operation. One specific method of normalization at the normalizing circuit 54 that can be easily implemented uses an analog to digital converter and a microprocessor to perform the division process. With extremely uniform glass containers (i.e., uniform wall thickness and no abrupt shape changes) the normalizing circuit 54 may not be necessary and the filtered detector signals input directly to the threshold circuit 55. This input signal will be converted into a digital level signal by comparing the amplitude with some pre-determined threshold level. In the embodiment shown in FIG. 10 the threshold level is indicated as being programmable so that the level can be changed as a function of the beam position within the glass container through the beam scan position logic 56. Varying the threshold level can provide a unique accept/reject sensitivity for different parts of the container as deemed necessary by the inspection criteria. In the logic signal processor the multiple detector signals are combined to produce a response only for contaminant particles or hazardous glass conditions. To optimize the logic processing, a programmable logic network would be used so that the processing response is dependent on the optical beam location within the glass container. A logical combination of the detector signals DS can be used to eliminate structural noise, such as high reflection from corner areas without losing detection sensitivity. One technique for a three-detector system was illustrated previously in FIG. 5. For bottle areas where no structural noise exists (such as the flat bottom of the container) then a signal from any one detector may be used independently as a reject indicator. Other logic operations which may be implemented include a sequential production of a signal from a single detector within a specific time (equal to the scan period) before a "flaw" condition is produced. Here the optical system would require multiple interruptions of the scanned beam and a contaminant particle. This multiple detection logic will be effectively used in reducing the uncertainty region between "accept" and "reject" conditions. These two signal processing methods are illustrated in FIG. 10 which can be easily understood by one skilled in the art of circuit design. In the interior part of a bottle, where little structural noise is encountered, the direct combination of detector signals 57 would be used. For the corner and wall areas where labels exist, the coincidence processing 61 would be used while for the central portion of the bottle bottom, individual detector or coincidence detector 57 or 61 response could be used. The delay module 62 requires that a defect be detected by more than one beam crossing. This delay module would delay a pulse 59 exactly one scan period of time. By logically combining the delayed pulse with the succeeding pulse, a flaw must be intercepted two times to produce a valid flaw signal 60. Signals 58 and 59 produce a flaw signal 60 only when both are present at the input of the logic module.

Various portions of FIG. 10 can be used for inspecting different parts of a semitransparent container using the beam position logic module 56 to control the detector signal flow through the signal processor.

What is claimed is:

1. An electro-optic inspection system for detecting defects on or in a transparent or semitransparent container, which comprises: a means for generating a polarized optical beam which illuminates hazardous and contaminant materials in said container; and a polarized optical beam detector system for detecting light scattered from said hazardous and contaminant materials, wherein said polarized optical beam detector system comprises a polaroid element to reject light from said container, said polaroid element having a polarization whose direction is different from that of the polarization of light reflected from said container itself, a Fresnel lens optical system to increase collection field angle of a photo-multiplier detector, a diffuser for scattering an image light, and a band-pass filter for reducing an ambient light level reaching said photo-multiplier detector, said polaroid element, said Fresnel lens optical system, said diffuser and said band-pass filter being disposed in such a manner that the light passes them in the stated order.

2. An electro-optic inspection system for detecting defects on or in a transparent or semitransparent container, which comprises: a means for generating a scanned, polarized optical beam to illuminate hazardous and contaminant materials in said container; and multiple optical detectors with a logical combination of detector signals for eliminating false flaw signals due to the structure of said container and producing one accept/reject status signal, wherein each of said optical detectors comprises a polaroid element having a polarization whose direction is different from that of the polarization of light reflected from the container itself thereby to reject light from said container, a Fresnel lens optical system to increase collection field angle of a photo-multiplier detector, a diffuser for scattering an image light, and a band-pass filter for reducing an ambient light level reaching said photo-multiplier detector, said polaroid element, said Fresnel lens optical system, said diffuser and said band-pass filter being disposed in such a manner that the light passes them in the stated order.

3. An electro-optic inspection system according to claim 2, wherein said scanned optical beam is either blocked or scattered by hazardous or contaminant materials and there is provided with a logic network which combines outputs of said multiple optical detectors to produce one accept/reject status signal.

4. An electro-optic inspection system according to claim 2, wherein said multiple optical detectors use depolarizing properties of said hazardous and contaminant materials to indicate their presence within said container.

5. An electro-optic inspection system according to claim 2, wherein said detectors are positioned around the container.

6. An electro-optic inspection system according to claim 2 wherein the logical combination produces a defect finding signals when the signals from more than one detector exceed the threshold level.

7. An electro-optic inspection system according to claim 6, wherein the logical combination also produces a defect signal when the signal from at least one detector exceeds the threshold level during the period when the optical beam is scanning the container area where no structural noise exists.

* * * * *